US008527030B2

(12) United States Patent
Van Zijl et al.

(10) Patent No.: US 8,527,030 B2
(45) Date of Patent: Sep. 3, 2013

(54) MICROVASCULAR BLOOD VOLUME MAGNETIC RESONANCE IMAGING

(75) Inventors: Peter C. M. Van Zijl, Ellicott City, MD (US); Hanzhang Lu, Baltimore, MD (US); Xavier Golay, Baltimore, MD (US)

(73) Assignee: Kennedy Krieger Institute, Baltimore, MD (US)

( * ) Notice: Subject to any disclaimer, the term of this patent is extended or adjusted under 35 U.S.C. 154(b) by 2066 days.

(21) Appl. No.: 10/525,699

(22) PCT Filed: Aug. 26, 2003

(86) PCT No.: PCT/US03/26580
§ 371 (c)(1),
(2), (4) Date: Feb. 22, 2005

(87) PCT Pub. No.: WO2004/021028
PCT Pub. Date: Mar. 11, 2004

(65) Prior Publication Data
US 2005/0215881 A1 Sep. 29, 2005

Related U.S. Application Data

(60) Provisional application No. 60/406,040, filed on Aug. 27, 2002.

(51) Int. Cl.
*A61B 5/05* (2006.01)
(52) U.S. Cl.
USPC .......................................... 600/410; 600/413
(58) Field of Classification Search
USPC ................ 600/410, 413; 324/306–307, 309, 324/300, 318, 322; 429/9.3
See application file for complete search history.

(56) References Cited

U.S. PATENT DOCUMENTS 4,942,359 A 7/1990 Sano ............................. 324/309
4,945,478 A * 7/1990 Merickel et al. ............... 382/131
(Continued)

FOREIGN PATENT DOCUMENTS

EP 0 297 832 A2 6/1988
WO WO 0057777 A1 * 10/2000

OTHER PUBLICATIONS

Song, H. K. et al.; "Multislice Double Inversion Pulse Sequence for Efficient Black-Blood MRI", MRM 47, 616-620 (2002).*

(Continued)

*Primary Examiner* — Long V. Le
*Assistant Examiner* — Bo J Peng
(74) *Attorney, Agent, or Firm* — Fay Sharpe LLP

(57) ABSTRACT

A magnetic resonance imaging system includes a magnetic resonance imaging scanner (10) that performs an inversion recovery magnetic resonance excitation sequence (70) having a blood-nulling inversion time (60) determined based on a blood T1 value appropriate for a selected magnetic field and blood hematocrit, whereby magnetic resonance of blood is substantially nulled. The inversion recovery excitation sequence (70) includes an inversion radio frequency pulse (74) applied with a small or zero slice-selective magnetic field gradient pulse to avoid inflow effects, and an excitation radio frequency pulse (80). The inversion pulse (74) and excitation pulse (80) are separated by the inversion time (60). The magnetic resonance imaging scanner (10) subsequently performs a readout magnetic resonance sequence (72) or spectroscopy sequence to acquire a magnetic resonance signal from tissue other than the nulled blood. A reconstruction processor (44) generates a reconstructed image from the acquired magnetic resonance signal.

18 Claims, 5 Drawing Sheets

(56) References Cited

U.S. PATENT DOCUMENTS

| | | | | |
|---|---|---|---|---|
| 5,221,899 | A | 6/1993 | Gonen et al. | 324/307 |
| 5,429,134 | A * | 7/1995 | Foo | 600/413 |
| 5,557,202 | A * | 9/1996 | Miyazaki et al. | 324/307 |
| 5,627,468 | A * | 5/1997 | Kojima et al. | 324/307 |
| 5,677,626 | A * | 10/1997 | Miyazaki et al. | 324/307 |
| 5,776,891 | A * | 7/1998 | Coon et al. | 514/10 |
| 6,198,958 | B1 * | 3/2001 | Ives et al. | 600/411 |
| 6,265,875 | B1 * | 7/2001 | Saranathan et al. | 324/314 |
| 6,370,416 | B1 * | 4/2002 | Rosenfeld | 600/410 |
| 6,462,542 | B1 * | 10/2002 | Venkataramanan et al. | 324/303 |
| 6,498,946 | B1 * | 12/2002 | Foo et al. | 600/410 |
| 6,589,506 | B2 * | 7/2003 | Cremillieux et al. | 424/9.3 |
| 7,254,437 | B2 * | 8/2007 | Miyazaki | 600/410 |
| 7,308,298 | B2 * | 12/2007 | Miyazaki | 600/410 |
| 7,412,279 | B2 * | 8/2008 | Weisskoff et al. | 600/420 |
| 7,546,155 | B2 * | 6/2009 | Foo et al. | 600/410 |
| 7,561,909 | B1 * | 7/2009 | Pai et al. | 600/410 |
| 2002/0165349 | A1 * | 11/2002 | Kirsch et al. | 530/350 |
| 2002/0169372 | A1 * | 11/2002 | Miyazaki | 600/410 |
| 2002/0188190 | A1 * | 12/2002 | Kassai et al. | 600/410 |
| 2003/0120151 | A1 * | 6/2003 | Constantinides | 600/431 |
| 2004/0059213 | A1 * | 3/2004 | Kassai et al. | 600/410 |
| 2004/0061496 | A1 * | 4/2004 | Ookawa | 324/307 |
| 2004/0105843 | A1 * | 6/2004 | Bernard et al. | 424/85.6 |
| 2005/0065430 | A1 * | 3/2005 | Wiethoff et al. | 600/413 |
| 2007/0038077 | A1 * | 2/2007 | Wiethoff et al. | 600/420 |
| 2007/0265522 | A1 * | 11/2007 | Kassai et al. | 600/411 |
| 2008/0021306 | A1 * | 1/2008 | Van Zijl et al. | 600/419 |

OTHER PUBLICATIONS

Van Zijl, P.C.M., et al., "Quantitative Assessment of Blood Flow, Blood Volume and Blood Oxygenation Effects in Functional Magnetic Resonance Imaging", Nature Medicine 4(2), 159-167 (1998).*

Mandeville, JB, et al., "Dynamic Functional Imaging of Relative Cerebral Blood Volume During Rat Forepaw Stimulation", MRM 39:615-624 (1998).

Kwong, KK, et al. "Dynamic Magnetic Resonance Imaging of Human Brain Activity During Primary Sensory Stimulation", Proc. Natl. Acad. Sci. USA 89:5675-5679 Jun. 1992.

van Zijl, PCM, et al., "Quantitative Assessment of Blood Flow, Blood Volume and Blood Oxygenation Effects in Functional Magnetic Resonance Imaging", Nature Medicine 4(2), 159-167 (1998).

Edelman, RR, et al. "Extracranial Carotid Arteries: Evaluation with "Black Blood" MR Angiography" Radiology 177:45-50 (1990).

Lu, H., et al. "Functional Magnetic Resonance Imaging Based on Changes in Vascular Space Occupancy", MRM 50:263-274 (2003).

* cited by examiner

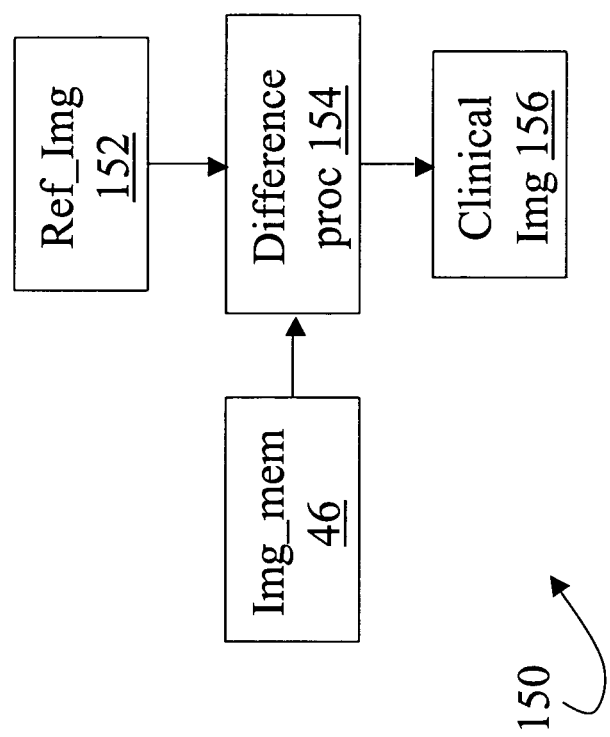

MICROVASCULAR BLOOD VOLUME MAGNETIC RESONANCE IMAGING

BACKGROUND OF THE INVENTION

The following relates to the diagnostic imaging arts. It finds particular application in non-invasive measurement by magnetic resonance imaging of cerebral blood volumes, and will be described with particular reference thereto. However, it also finds application in measurement by magnetic resonance imaging of blood volumes in other tissues.

In-situ measurement of blood volume is useful in various clinical, diagnostic, and research applications. Local cerebral blood volume changes, for example, correlate with local neuronal activity in the brain. Cerebral blood volume measurements during physiological stimulation thus provides a tool for functional studies of brain activity. Cerebral blood volume measurements can also provide information about impaired and/or damaged tissue in stroke victims, as well as about lesions in many disorders, including, but not limited to cancer, vascular disorders, and the like. Blood volume imaging of other organs besides the brain can similarly provide functional and diagnostic data that is useful in clinical studies, diagnoses, and tests (e.g. stress tests or tests of vascular compliance).

Various imaging modalities have been used to measure blood volume characteristics, including positron emission tomography, single photon emission computed tomography, and magnetic resonance imaging. Most of these are invasive approaches, in which the subject is administered a suitable contrast agent that selectively enhances blood contrast in the selected imaging modality. For magnetic resonance imaging, various paramagnetic contrast agents are commonly used for this purpose. The requirement of an administered contrast agent is a substantial disadvantage of these techniques.

Magnetic resonance imaging of blood oxygenation level dependence (BOLD) is a non-invasive technique for indirectly measuring blood volume. In this technique, blood hemoglobin is used as an endogenous contrast agent. In one BOLD imaging approach, magnetic resonance imaging is performed as a function of physiological stimulation that causes changes in blood oxygenation level. Blood volume is estimated from BOLD measurements by making assumptions pertaining to other parameters that affect blood oxygenation level, such as blood flow. Hence, BOLD does not provide a direct measure of the blood volume.

A disadvantage of both the invasive techniques and the BOLD techniques as applied to blood volume measurement is that these existing techniques generally do not differentiate between blood in large blood vessels, on the one hand, and perfused blood in small capillaries or other microvessels, on the other hand. The blood volume in larger blood vessels is principally controlled by sympathetic regulation. In contrast, blood volume in microvessels having typical diameters of less than about 200 microns tends to vary to maintain local homeostasis or in response to chemicals such as vasodilators or vasorestrictive compounds. Consequently, the blood volume of microvessels responds to physiological perturbations such as local neuronal activity. For functional magnetic resonance imaging, the volume of blood in the microvessels is typically of principle interest, while the blood signal from larger blood vessels is interfering and thus undesirable. On the other hand, total microvascular plus macrovascular blood volume may change in some diseases, including but not limited to for instance arteriovenous malformations.

The present invention contemplates an improved apparatus and method that overcomes the aforementioned limitations and others.

BRIEF SUMMARY OF THE INVENTION

According to one aspect, a magnetic resonance imaging method is provided. A blood-nulling magnetic resonance excitation sequence is performed that substantially nulls a magnetic resonance signal from blood. Subsequent to the performing of the blood-nulling magnetic resonance excitation sequence, a readout magnetic resonance sequence is performed to acquire a magnetic resonance signal from tissue other than the nulled blood.

According to another aspect, a magnetic resonance system is disclosed. A blood nulling means is provided for performing a blood nulling magnetic resonance excitation sequence that substantially nulls a magnetic resonance signal from blood. A readout means is provided for performing a readout magnetic resonance sequence to acquire a magnetic resonance signal from tissue other than the nulled blood, the readout means operating subsequent to operation of the blood nulling means.

One advantage resides in measuring the parenchymal vascular space occupancy, which is more sensitive to physiological perturbations than is the total vascular volume which includes the large blood vessels.

Another advantage resides in providing measurements of the absolute blood volume.

Yet another advantage resides in providing images with substantially nulled blood magnetic resonance signal, i.e. a blood signal reduction sufficient to have MRI signal remaining that is predominantly from other tissues.

Numerous additional advantages and benefits will become apparent to those of ordinary skill in the art upon reading the following detailed description of the preferred embodiments.

BRIEF DESCRIPTION OF THE DRAWINGS

The invention may take form in various components and arrangements of components, and in various process operations and arrangements of process operations. The drawings are only for the purpose of illustrating preferred embodiments and are not to be construed as limiting the invention.

In FIG. 2, the time intervals TI, TE, TR are not drawn to scale.

FIG. 5 shows a block diagram of a processor for computing a difference image having enhanced contrast for vascular space occupancy abnormalities.

DETAILED DESCRIPTION OF THE PREFERRED EMBODIMENTS

Figure 1:
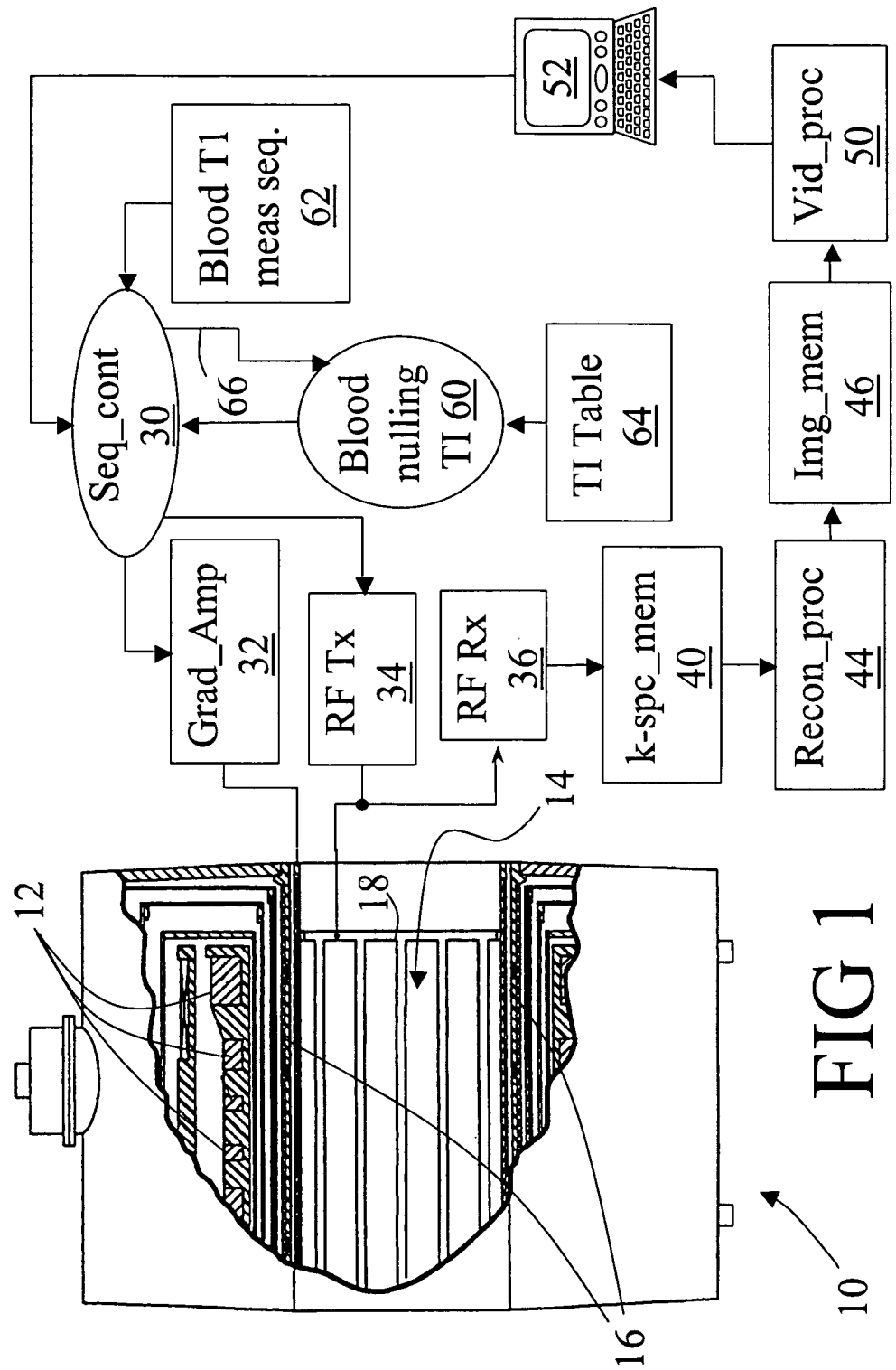
FIG. 1 diagrammatically shows a magnetic resonance imaging system for measuring vascular space occupancy.

With reference to FIG. 1, a magnetic resonance imaging scanner 10 includes main magnet coils 12, which are preferably superconducting coils, although resistive main magnet coils or a permanent magnet can also be employed. The main magnet coils 12 are energized to generate a substantially uniform main magnetic field in an examination region 14. Magnetic field gradient coils 16 produce gradients in selected spatial directions to spatially encode magnetic resonances that are generated by energizing a radio frequency coil 18. In FIG. 1, a whole-body radio frequency coil 18 is shown; however, local coils such as head coils, phased radio frequency coil arrays, SENSE coils, and the like can be used instead of or in conjunction with the whole-body radio frequency coil 18 to excite magnetic resonances and/or to detect magnetic resonance echoes.

A magnetic resonance sequence controller 30 coordinates and controls a radio frequency transmitter 34 that is coupled to the whole-body radio frequency coil 18 or another radio frequency coil to excite magnetic resonance echoes, and controls magnetic field gradient controllers 32 coupled to the gradient coils 16 to spatially encode the excited magnetic resonance echoes. One or more radio frequency receivers 36 coupled to the whole-body radio frequency coil 18 or another radio frequency coil detects, demodulates, and digitizes the magnetic resonance echoes and stores digital magnetic resonance samples in a k-space memory 40. A reconstruction processor 44 performs a Fourier transform-based image reconstruction or other type of image reconstruction to generate one or more reconstructed images from the stored k-space magnetic resonance samples.

The reconstructed images are stored in an image memory 46, processed by a video processor 50 and displayed on a user interface 52, transmitted over a local computer network or the Internet, or otherwise processed. Preferably, the user interface 52 includes a display, printer, or other output device that allows a radiologist or other operator to view, render, or otherwise manipulate the reconstructed images. Moreover, the user interface 52 preferably enables the radiologist or other operator to communicate with the magnetic resonance sequence controller 30 to create magnetic resonance imaging sequences, modify imaging sequences, execute imaging sequences, or otherwise control the magnetic resonance imaging scanner 10.

With continuing reference to FIG. 1, for clinical or diagnostic applications in which the blood volume is of interest, a measure of the vascular space occupancy (VASO) is performed. The approach uses an inversion recovery magnetic resonance excitation sequence having an inversion time 60 optimized for substantial nulling of the blood signal based on a blood T1 value particular to a certain magnetic field strength and hematocrit range. The inversion recovery magnetic resonance excitation sequence substantially nulls the signal from blood so that the magnetic resonance signal corresponds predominantly to tissue, with substantially negligible contribution of blood. This approach takes advantage of a substantial independence of the T1 value of blood on blood oxygenation, which allows the inversion recovery blood nulling to be operative for different types of vessels (arterial, arteriolar, capillary, venular, and venous) as well as throughout a physiological perturbation cycle.

A suitable value for the inversion time (TI) 60 for nulling blood can be obtained in a number of ways. In one suitable approach, a blood T1 measuring sequence 62 is applied by the sequence controller 30 to measure a T1 value of a representative blood sample using a blood perfusion apparatus, and the inversion time (TI) 60 is computed therefrom. Alternatively, a major blood vessel can be identified in a reconstructed image, and a direct measurement of the T1 value of blood inside the identified blood vessel is obtained using conventional magnetic resonance imaging sequences. In another approach, as it has been found in practice that the T1 of blood is generally not subject-dependent for most human subjects having substantially normal blood, suitable inversion times (TI) can be computed from measurements of a representative blood sample of substantially normal human blood or of animal blood of suitable mammalian origin and collected in a table 64, such as Table I and Table II contained herein. These values are generally suitable for substantially normal human blood, and include inversion time dependence upon the main magnetic field strength (Table I providing values for a 1.5 T field, and Table II providing values for a 3.0 T field) and on the sequence repeat time (TR). Rather than employing tabulated data, the inversion time 60 can be related to magnetic field strength, repeat time TR, and optionally other parameters by an empirical functional relationship or other suitable relationship. The tabulated TI values are preferably used as a guideline for determining an inversion time TI that substantially nulls blood so that signals are predominantly from tissue. The tabulated values do not exclude other TI values that can also accomplish blood nulling.

TABLE I

Optimal inversion times (TI) for blood at 1.5 Tesla magnetic field

| TR (ms) | optimal TI (ms) | remaining gray signal |
|---|---|---|
| 1000 | 409.4499457 | 0.039848653 |
| 1500 | 551.5765181 | 0.07104825 |
| 2000 | 659.2454703 | 0.100852361 |
| 2500 | 738.9402994 | 0.126845436 |
| 3000 | 796.8489702 | 0.148292976 |
| 3500 | 838.3345867 | 0.165337186 |
| 4000 | 867.7421743 | 0.178518564 |
| 4500 | 888.427932 | 0.188505318 |
| 5000 | 902.8982691 | 0.195951912 |
| 5500 | 912.9810254 | 0.20143462 |
| 6000 | 919.987164 | 0.205430439 |
| 6500 | 924.8460607 | 0.208318508 |
| 7000 | 928.2112602 | 0.21039169 |
| 7500 | 930.5397637 | 0.21187148 |
| 8000 | 932.1498927 | 0.212922716 |
| 8500 | 933.262774 | 0.213666531 |
| 9000 | 934.0317304 | 0.214191053 |
| 9500 | 934.5629341 | 0.214559874 |

TABLE II

Optimal inversion times (TI) for blood at 3.0 Tesla magnetic field

| TR (ms) | optimal TI (ms) | remaining gray signal |
|---|---|---|
| 1000 | 424.6207165 | 0.029639854 |
| 1500 | 583.5056824 | 0.054873106 |
| 2000 | 711.232168 | 0.080671988 |
| 2500 | 812.0982526 | 0.1047927 |
| 3000 | 890.5574158 | 0.126155559 |
| 3500 | 950.8320255 | 0.144394456 |
| 4000 | 996.6759107 | 0.159557069 |
| 4500 | 1031.270597 | 0.171909777 |
| 5000 | 1057.21771 | 0.18181485 |
| 5500 | 1076.588295 | 0.189656765 |
| 6000 | 1090.998208 | 0.195801064 |
| 6500 | 1101.689382 | 0.20057404 |
| 7000 | 1109.605744 | 0.204255213 |
| 7500 | 1115.458796 | 0.207077192 |
| 8000 | 1119.781556 | 0.209229423 |
| 8500 | 1122.971521 | 0.210863669 |
| 9000 | 1125.324122 | 0.212099926 |
| 9500 | 1127.058395 | 0.21303208 |

An inversion time adjustment is optionally performed to compensate for deviation in blood T1 value resulting from abnormal hematocrit values, sickle-cell pathologies, or another blood abnormality of a specific imaging subject. In one suitable adjustment technique, the blood-nulling inversion recovery imaging sequence is performed for several inversion times around the blood nulling inversion time selected from Tables I and II, and the blood nulling inversion time 60 is selected as the inversion time providing substantially negligible image signal from a large blood vessel. A data flow line 66 in FIG. 1 corresponds to selecting the blood nulling inversion time 60 based on magnetic resonance measurements performed using the scanner 10.

Figure 2:
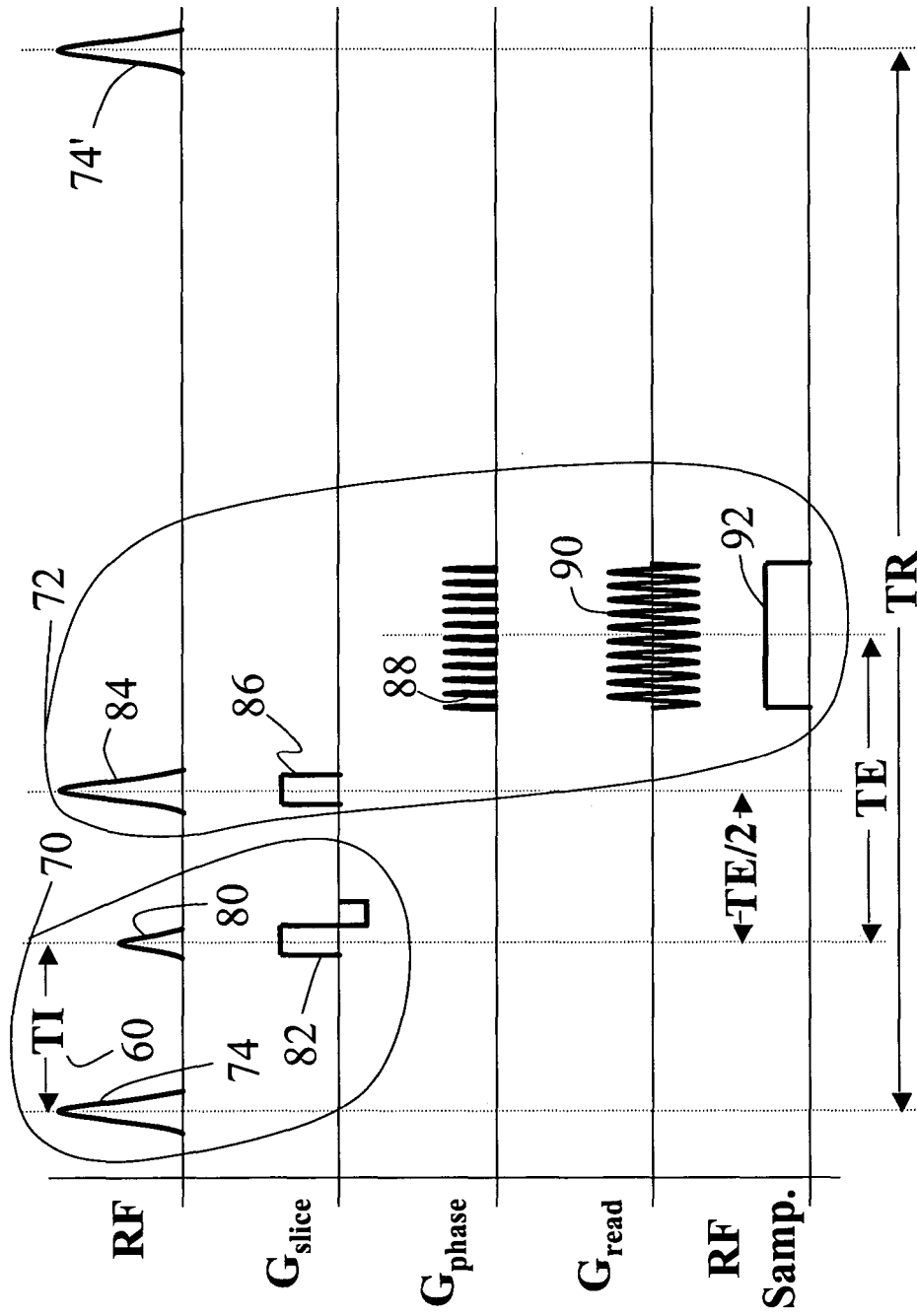
FIG. 2 diagrammatically shows a magnetic resonance imaging pulse sequence employing inversion recovery to null the blood signal.

FIG. 2 diagrammatically shows a suitable magnetic resonance imaging pulse sequence employing a blood-nulling inversion recovery magnetic resonance excitation sequence 70 to null the blood signal, and an exemplary single shot echo planar imaging readout 72. Note that the echo planar imaging readout is exemplary only, and does not exclude employing additional or other magnetic resonance imaging, magnetic resonance spectroscopy or localized spectroscopy detection schemes. For example, the readout sequence 72 can be a single-shot imaging sequence, a single-shot echo planar sequence, a multi-shot imaging sequence, a spectroscopy sequence, a multiple slice image, a one-dimensional, two-dimensional, or three dimensional spatial encoding sequence, a fractional k-space acquisition sequence, a spin echo readout sequence, a gradient echo readout sequence, or the like.

Looking first at the inversion recovery excitation sequence 70, an inversion pulse 74 is applied to invert the spins. Preferably, the inversion pulse 74 is a 180° pulse implementing a 180° flip angle for the spins. In this case, the inversion time TI 60 is substantially representative to induce proper blood signal reduction based on the T1 value of blood for the particular experimental conditions (field, hematocrit, oxygenation, etc). It is also contemplated, however, to use an inversion pulse having a flip angle greater than 90° but other than 180°, in which case the appropriate inversion time TI 60 is readily computed from the proper T1 and acquisition parameters such as the repetition time TR. In general, the inversion time TI 60 is selected as a time during which the longitudinal component of the flipped spins of blood decay from the flip angle to the crossover or null position. The null condition corresponds to a zero-crossing point of the longitudinal spin component; as the longitudinal spin component decays from the flipped or inverted alignment back toward the normal, non-inverted alignment it passes through a point where the longitudinal component passes substantially through zero, that is, the longitudinal spin component through a substantially zero crossing point. Substantially zero is understood to correspond to a substantially negligible blood signal such that the acquired magnetic resonance signal predominantly contains signals from tissues other than blood.

Preferably, the inversion pulse 74 is not accompanied by a spatial encoding magnetic field gradient pulse or is accompanied by a relatively small spatial encoding magnetic field gradient pulse. This ensures that the spins of blood throughout the subject region of interest reach the null condition after the inversion time delay TI 60. In particular, the blood nulling is independent of blood flow since the blood-nulling inversion pulse 74 is spatially non-selective or selects a relatively large region. Thus, flowing blood that flows into the slice of interest at the time of excitation or at the time of readout is nulled appropriately.

At the blood null condition, that is, after a delay time corresponding to the inversion time TI 60, an excitation pulse 80 is applied in conjunction with a slice-selective magnetic field gradient pulse 82 to excite spins in a selected slice of the subject region of interest. The excitation pulse 80 is preferably a 90° excitation pulse having a flip angle of 90°; however, an excitation pulse with other than a 90° flip angle is also contemplated. Because the blood is in a null condition at the time the excitation pulse 80 is applied, negligible magnetic resonance signal is excited in the nulled blood by the excitation pulse 80. Tissue such as fat, gray and white brain tissues, and the like generally have a different T1 value from that of blood, and so these tissues are not at a null condition at the time the excitation pulse 80 is applied. Hence, the excitation pulse 80 excites magnetic resonance predominantly in tissue.

The exemplary single shot echo planar imaging readout 72 samples the magnetic resonance excited in the tissue by the excitation pulse 80. The illustrated single shot echo planar imaging readout 72 is a conventional readout including a 180° spin refocusing radio frequency pulse 84 and slice-selective gradient pulse 86 that create a spin echo in a selected slice at a time-to-echo interval TE after the excitation pulse 80. A series of phase-encoding magnetic field gradient pulses 88 and a generally sinusoidal read magnetic field gradient waveform 90 step through a grid of k-space values in the selected slice while the radio frequency receiver 36 of FIG. 1 performs sampling 92 of the spin echo. The magnetic resonance signal k-space samples are stored in the k-space memory 40 of FIG. 1 and are processed to produce a reconstructed image representation as described previously.

The single shot echo planar imaging readout 72 shown in FIG. 2 is exemplary only. Substantially any type of magnetic resonance imaging or magnetic resonance spectroscopy readout or acquisition sequence can be employed. For imaging applications, the readout sequence may be a fast, single-shot sequence that acquires at least one slice per excitation. For example, the exemplary single shot echo planar imaging readout 72 can be replaced by a short gradient echo readout sequence. An echo time (TE) of the readout shown in FIG. 2 is preferably kept short so that the readout is performed while the blood remains substantially in the nulled condition and to minimize contributions such as those from the blood-oxygen-level-dependent (BOLD) effect. Optionally, one or more additional inversion pulses are applied to keep the blood close to the null condition during longer readout sequences.

Although the inversion recovery blood-nulling sequence 70 is preferred, other pulse sequences can be employed to substantially null the blood signal so that the magnetic resonance is predominantly due to tissues other than blood. For example, the use of a long echo time (TE) at high magnetic field produces a substantially blood-nulled signal; however, in sequences of this type the extravascular blood oxygenation level dependence (BOLD) contribution is large, complicating determination of other physiological parameters such as cerebral blood volumes (CBV) and the like. In one suitable approach for overcoming this large BOLD effect, the CBV contribution is quantified from interpolation of the TE dependence from a series of TE values at sufficiently long TE to avoid intravascular contributions that would occur at shorter TE and/or from differences between such interpolations under different physiological conditions or between normal and diseased tissue.

The blood-nulling magnetic resonance sequence of FIG. 2 is optionally repeated with a repetition time (TR) to acquire reconstructed images for multiple slices or for multiple three-dimensional (3D), two-dimensional (2D), or one-dimensional (1D) spatial encodings, for example to obtain a three-dimensional reconstructed image volume. In FIG. 2, an exemplary succeeding spatially non-selective inversion recovery pulse 74' corresponds to the beginning of the next repetition of the blood-nulling imaging sequence. Optionally, because the blood nulling establishes a substantially negligible blood signal, it is possible to acquire multiple slices or multiple 1D, 2D, or 3D spatial encodings per single nulling condition. This applies to both imaging and spectroscopy applications.

Reconstructed images acquired using inversion-recovery blood-nulling magnetic resonance sequences such as the exemplary sequence of FIG. 2 can be used in various ways. For example, while it is known in the art to process a reconstructed image to determine proton density ($\rho$), T1, and T2 weightings, the determined weighting values are typically composite values having contributions from both blood and tissue. By applying substantially the same processing to the blood-nulled reconstructed images, more accurate $\rho$, T1, and T2 weightings for tissue can be obtained without interference from the blood signal.

Optionally, other tissues are nulled in addition to blood, to minimize contributions from those other tissues or components. For example, such combined blood and tissue nulling can be used to largely isolate a magnetic resonance signal from cerebral spinal fluid (CSF) in the brain.

Reconstructed images acquired using inversion-recovery blood-nulling magnetic resonance sequences contain information pertaining to vascular space occupancy insofar as the images includes contributions from tissue but substantially exclude contributions from the blood volume. By applying a physiological perturbation, the blood volume can be changed. For example, cerebral blood volume undergoes vasodilation responsive to visual stimulation and breath-hold. Similarly, cerebral blood volume undergoes vasoconstriction responsive to hyperventilation. Blood volume changes can also be induced by administration of a selected drug, for example, but not limited to, for stress testing or the assessment of vascular compliance. Moreover, certain diseases such as cardiac ischemia, stroke, cancer, vascular deformations, and the like, represent a chronic or transient physiological perturbation that can cause a change in blood volume detectable with the methodology described herein.

In most of the above cases, the change in blood volume occurs principally in the microvessels rather than in the large vessels and parenchyma. Advantageously, the blood volume changes measured using the blood-nulled reconstructed images reflect the parenchymal blood volume (denoted BV herein) which substantially corresponds to the volume of the microvessels without contributions from the larger vessels. In contrast, vascular volume effects measured by BOLD and many other existing techniques include the large vessels and parenchyma and other tissues close to these vessels (for example, cerebral spinal fluid). For parenchymal tissue (tissue with perfused blood), the parenchymal vascular space occupancy (VASO, also denoted $\xi$ herein) is given by:

$$\xi = \frac{BV}{BV + V_{tissue}} = \frac{BV}{V_{par}}, \quad (1)$$

where BV is the blood volume, $V_{tissue}$ is the pure tissue volume (without blood), and $V_{par}$ is the volume of the parenchymal tissue, that is, $V_{par}=BV+V_{tissue}$. The measured parenchymal vascular space occupancy $\xi$ advantageously is more sensitive to physiological perturbation, including permanent disease-induced perturbation, than is the total vascular volume. Changes in large-vessel volume (that is, outside parenchymal regions) are also accessible by the blood nulling approach. At appropriate resolution, changes in large-vessel volume do not interfere with the indicated parenchymal blood volume changes due to the applied spatial encoding.

For parenchymal tissue, the magnetic resonance signal (denoted by S herein) is proportional to a sum of the magnetization contributions of the microvessels and of the pure tissue. In general, the total signal $S_{par}$ from the parenchymal tissue (including both tissue and perfused blood) can be written as:

$$S_{par}=S_{blood}+S_{tissue} \quad (2),$$

where $S_{blood}$ and $S_{tissue}$ are the blood and tissue signals, respectively. Inserting the vascular space occupancy $\xi$ and water density factors $C_{par}$ and $C_{blood}$ for parenchymal tissue and blood, respectively, into Equation (2) yields:

$$S_{par} \cong C_{blood} \cdot \xi \cdot M_{blood} \cdot e^{-TE/T2_{blood}} + (C_{par} - \xi \cdot C_{blood}) \cdot M_{tissue} \cdot e^{-TE/T2_{tissue}} \quad (3),$$

where $T2_{blood}$ and $T2_{tissue}$ tissue are suitable time constants for the exemplary spin echo readout 72 of FIG. 2 due to the spin refocusing produced by the radio frequency pulse 84. For a gradient echo readout, the T2 values should be replaced by T2* values in Equation (3). The terms $M_{blood}$ and $M_{tissue}$ correspond to the initial transverse magnetization of the blood and the tissue, respectively, produced by the excitation radio frequency pulse 80. As a consequence of using the blood-nulling excitation sequence 70, however, the term $M_{blood}$ corresponding to the blood is substantially zero, and so Equation (3) reduces to:

$$S_{par} \cong (C_{par} - \xi \cdot C_{blood}) \cdot M_{tissue} \cdot e^{-TE/T2_{tissue}} \quad (4).$$

A fractional parenchymal signal change $\Delta S/S$ occurring responsive to a physiological perturbation, defined as:

$$\frac{\Delta S}{S} = \frac{S_{par}^{act} - S_{par}^{rest}}{S_{par}^{rest}}, \quad (5)$$

can be written by combining Equations (4) and (5) as:

$$\frac{\Delta S}{S} = \frac{(C_{par} - \xi^{act} \cdot C_{blood}) \cdot e^{-TE/T2_{tissue}^{act}} - (C_{par} - \xi^{rest} \cdot C_{blood}) \cdot e^{-TE/T2_{tissue}^{rest}}}{(C_{par} - \xi^{rest} \cdot C_{blood}) \cdot e^{-TE/T2_{tissue}^{rest}}}, \quad (6)$$

where the superscript "act" references the perturbed state and the superscript "rest" references the unperturbed rest state or another suitable reference state. Dividing the numerator and denominator of Equation (6) by $C_{par}e^{-TE/T2(tissue,rest)}$, the fractional parenchymal signal change $\Delta S/S$ can be written as:

$$\frac{\Delta S}{S} = \frac{\left(1 - \xi^{act} \cdot \frac{C_{blood}}{C_{par}}\right) \cdot e^{-TE/(1/T2_{tissue}^{act} - 1/T2_{tissue}^{rest})} - \left(1 - \xi^{rest} \cdot \frac{C_{blood}}{C_{par}}\right)}{\left(1 - \xi^{rest} \cdot \frac{C_{blood}}{C_{par}}\right)}, \quad (7)$$

Making use of the series expansion approximation $e^x \sim 1+x$ and defining an apparent change in transverse relaxation rate of tissue $\Delta R2$ as:

$$\Delta R2 = \frac{1}{T2_{tissue}^{act}} - \frac{1}{T2_{tissue}^{rest}}, \quad (8)$$

Equation (7) can be rewritten as:

$$\frac{\Delta S}{S} = \frac{\xi^{act} \cdot \frac{C_{blood}}{C_{par}} \cdot \Delta R2 \cdot TE + \xi^{rest} \cdot \frac{C_{blood}}{C_{par}}}{\left(1 - \xi^{rest} \cdot \frac{C_{blood}}{C_{par}}\right)}. \quad (9)$$

Defining a rate of change $\Delta\xi$ of the vascular space occupancy as $\Delta\xi = \xi^{act} - \xi^{rest}$ and neglecting the term $\xi^{act}(C_{blood}/C_{par})\Delta R2$ TE in Equation (9) and simplifying yields:

$$\frac{\Delta S}{S} = \frac{-\Delta R2 \cdot TE - \Delta\xi \cdot \frac{C_{blood}}{C_{par}}}{\left(1 - \xi^{rest} \cdot \frac{C_{blood}}{C_{par}}\right)}. \quad (10)$$

Figure 3:
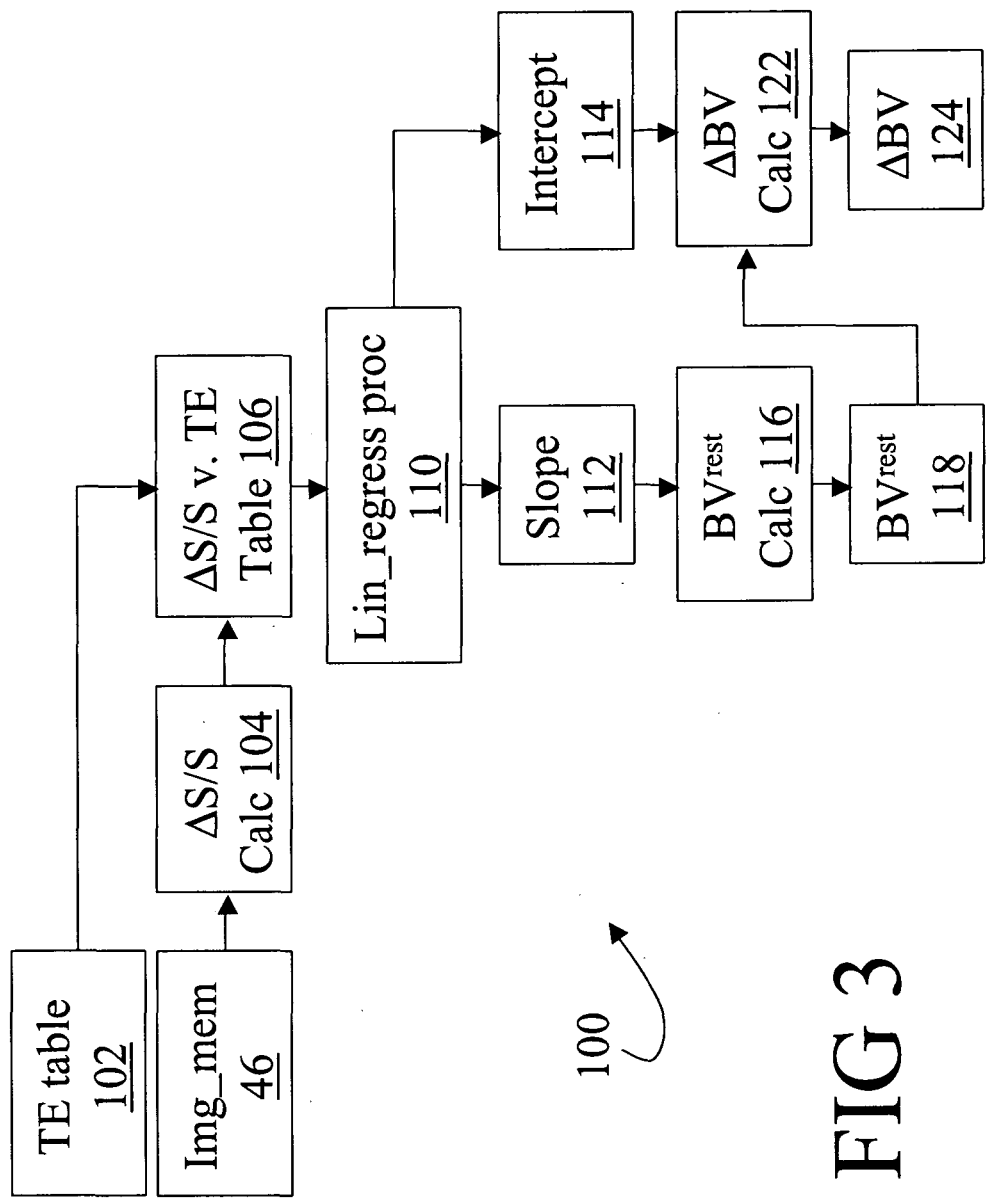
FIG. 3 shows a block diagram of a processor for computing a blood volume at rest and a blood volume change occurring responsive to a physiological perturbation.

FIG. 3 shows a block diagram of an exemplary processor 100 that computes a rest blood volume $BV^{rest}$ and a blood volume change $\Delta BV$ based on Equation (10). The processor 100 receives imaging data input from the image memory 46. The imaging data includes images taken at a plurality of echo times TE 102 with the imaging subject at rest, and corresponding images taken at the plurality of (that is, two or more) echo times TE with the imaging subject in a perturbed state. A processor 104 computes the fractional signal difference $\Delta S/S$ between the image of the subject in the rest state and the image of the subject in the perturbed state for each echo time TE to form a table 106 of fractional signal difference $\Delta S/S$ versus echo time TE. Recognizing that Equation (10) is a linear equation in echo time TE, a linear regression processor 110 computes a slope 112 and an ordinate-intercept 114 of the $\Delta S/S$ v. TE relationship.

A rest blood volume $BV^{rest}$ calculator 116 computes the rest blood volume $BV^{rest}$ 118 from the slope 112 according to:

$$slope = \frac{-\Delta R2}{1 - \xi^{rest} \cdot \frac{C_{blood}}{C_{par}}} = \frac{-\Delta R2}{1 - \frac{BV^{rest}}{V_{par}} \cdot \frac{C_{blood}}{C_{par}}}, \quad (11)$$

where Equation (11) is the slope component of the linear relationship between $\Delta S/S$ and TE of Equation (10). The rightmost side of Equation (11) is written with the rest parenchymal vascular space occupancy $\xi^{rest}$ replaced by blood volume $BV^{rest}$ divided by the volume $V_{par}$ of the parenchymal tissue under consideration in accordance with Equation (1). The $BV^{rest}$ calculator 116 uses literature values for the water density factors $C_{par}$ and $C_{blood}$, the known volume $V_{par}$ of the parenchymal tissue under consideration, and a value for $\Delta R2$ calculated from $T2_{tissue,act}$ and $T2_{tissure,rest}$ values obtained by fitting the signal value S at several echo times TE for each of the perturbed and rest states, respectively. If $V_{par}$ is unknown, the method can be used to determine the absolute blood volume fraction or vascular space occupancy ($\xi^{rest}$).

A blood volume change $\Delta BV$ calculator 122 computes the blood volume rate of change $\Delta BV$ 124 from the ordinate-intercept 114 according to:

$$Intercept = \frac{-\left(\frac{\Delta BV}{V_{par}} \cdot \frac{C_{blood}}{C_{par}}\right)}{\left(1 - \frac{BV^{rest}}{V_{par}} \cdot \frac{C_{blood}}{C_{par}}\right)}, \quad (12)$$

where Equation (12) is the ordinate-intercept component of the linear relationship between $\Delta S/S$ and TE of Equation (10) written with the rest parenchymal vascular space occupancy $\xi^{rest}$ replaced by $BV^{rest}/V_{par}$ and the change in vascular space occupancy $\Delta\xi$ is replaced by $\Delta BV/V_{par}$. The $\Delta BV$ calculator 122 uses literature values for the water density factors $C_{par}$ and $C_{blood}$, the known volume $V_{par}$ of the parenchymal tissue under consideration, and the rest blood volume $BV_{rest}$ 118 computed by the $BV^{rest}$ calculator 116. Alternatively, the absolute blood volume fraction or vascular space occupancy ($\xi^{rest}$) can be used if $V_{par}$ is unknown.

Figure 4:
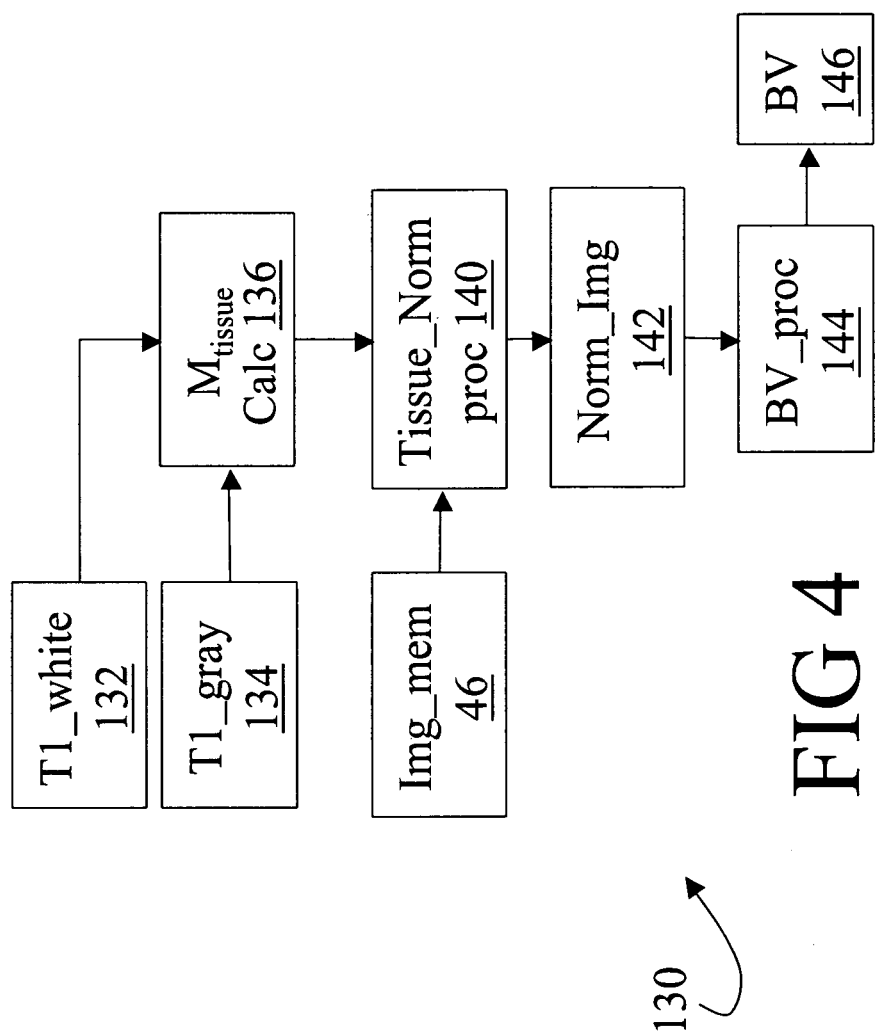
FIG. 4 shows a block diagram of a processor for computing absolute blood volume using a reconstructed image acquired with the blood signal nulled by an inversion recovery preparation.

FIG. 4 shows a block diagram of another processor 130 that computes an absolute blood volume BV. Computation of BV by the processor 130 is not based on a transient response to a physiological perturbation. Rather, data from the image memory 46, which may be a single image, is processed using Equation (4). The image is preferably acquired using a short echo time TE, so that the term $\exp(-TE/T2_{tissue})$ in Equation (4) is suitably approximated as unity so that the signal S is given by:

$$S_{par} \cong \left(C_{par} - \frac{BV}{V_{par}} \cdot C_{blood}\right) \cdot M_{tissue}, \quad (13)$$

where the parenchymal vascular space occupancy $\xi$ is replaced by the expression in Equation (1). The value of $M_{tissue}$ at the inversion time TI 60 is related to longitudinal tissue relaxation time $T1_{tissue}$ according to:

$$M_{tissue}(TI) = 1 - 2e^{-TI/T1_{tissue}} + e^{TR/T1_{tissue}} \quad (14),$$

where TR is the repetition time of the pulse sequence (indicated, for example, in FIG. 2). A suitable value for $T1_{tissue}$ can be measured using a known magnetic resonance technique such as saturation recovery pulse sequence and inversion recovery pulse sequence or, preferably, by a series of inversion pulses so that blood remains substantially nulled, while tissue signal decays with the representative $T1_{tissue}$. In the case of brain imaging, it is known that the $T1_{tissue}$ values for white and gray brain matter differ. Hence, as shown in FIG. 4 a $T1_{white}$ value 132 and a $T1_{gray}$ value 134 are preferably determined. Notice that $S_{par}$ also contains instrumental factors, for instance related to coil sensitivity and excitation homogeneity, the combined contribution of which we will call IF. This constant can also be determined during the T1 measurement from the voxels in ventricles, which only contains CSF and has a proton density very close to pure water. An $M_{tissue}$ processor 136 computes corresponding $M_{tissue}$ values at the inversion time TI 60 for white and gray brain matter, and a normalization processor 140 normalizes the image stored in the image memory 46 to produce a normalized image 142 according to:

$$S_{norm}(tissue) = \frac{S_{par}}{IF * M_{tissue}}, \quad (15)$$

where in Equation (15) the tissue magnetization $M_{tissue}$ is selected as the magnetization term corresponding to the T1$_{gray}$ value 134 for gray matter, and is selected as the magnetization term corresponding to the T1$_{white}$ value 136 for white matter. A blood volume processor 144 estimates the absolute blood volume BV 146 or the absolute blood volume fraction or vascular space occupancy ($\xi^{rest}$) by applying Equation (13) to the normalized image 142. For pure parenchyma, an additional approach to determine blood volume is to use the tissue T1 value to null the tissue and only look only at remaining blood. Using the same IF determined in the blood nulling experiment, the signal in such a tissue-nulled voxel at short TE is given by:

$$S_{norm}(\text{blood}) = \frac{S_{par}}{\text{IF} \cdot M_{blood}} = C_{blood} \cdot \xi \quad (16)$$

from which the BV (Equation (1)) and/or vascular space occupancy can be determined for known $C_{blood}$.

FIG. 5 shows a processor 150 that computes a clinical image from blood-nulled magnetic resonance images. The processor 150 is suitable in diagnostic applications for detecting an abnormality such as vasodilation or vasoconstriction caused by certain diseases such as cardiac ischemia, stroke, cancer, and the like. The image memory 46 stores an image of the imaging subject to be diagnosed. The image is compared with a reference image 152 by a difference processor 154 to generate a clinical image 156.

In one suitable approach, the difference processor 154 computes an absolute difference between the images, so that normal areas appear dark in the clinical image 156 whereas abnormal areas appear brighter in the clinical image 156 (or vice versa) due to differences between the subject image and the reference image in the vicinity of the abnormality. Optionally, the difference processor 154 computes a signed difference with a constant intensity level offset. In this approach, regions of vasodilation and regions of vasocontraction have opposite intensity polarities respective to the constant intensity level.

The reference image 152 can be obtained from various sources. For example, an image of a normal subject can be employed for the comparison. Alternatively, in the case of a bilaterally symmetric anatomical structure such as the brain, a contralateral image can be used. For example, a suspect right-side of the brain can be compared with a presumed normal left-side of the brain, preferably after a suitable left-right transposition of the contralateral comparison image. Still further, in cases of anatomical structures that are substantially homogeneous in the absence of an abnormality, a suspect portion of the organ can be compared with presumed normal portion of the same organ.

In the case of brain diagnoses, the normalized image 142 of FIG. 4 is optionally employed in the processor 150. The normalized image 142 advantageously has suppressed contrast between white matter regions and gray matter regions of the brain image, which makes the vascular space occupancy contrast more visible.

In some clinical applications, large vessels changes may occur in addition to microvascular changes. These can also be detected, and, at sufficient spatial resolution, can be separated from the microvascular changes.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A magnetic resonance method including:
   performing a magnetic resonance excitation sequence including a signal reduction component that reduces magnetization from blood more than magnetization from parenchymal tissue wherein the performing of a magnetic resonance excitation sequence includes performing an inversion recovery magnetic resonance excitation sequence having a spatially non-selective inversion recovery pulse followed by an excitation radio frequency pulse separated from the spatially non-selective inversion recovery pulse by an inversion time effective to reduce the magnetization from blood more than the magnetization from parenchymal tissue;
   subsequent to the performing of the magnetic resonance excitation sequence, performing a readout magnetic resonance sequence to acquire a magnetic resonance signal generated by the magnetic resonance excitation sequence including the blood signal reduction component; and
   determining a microvascular blood volume parameter based on the acquired magnetic resonance signal.

2. The magnetic resonance method as set forth in claim 1, wherein the performing of an inversion recovery magnetic resonance excitation sequence includes:
   applying the spatially non-selective inversion radio frequency pulse;
   delaying for the inversion time
   applying the excitation radio frequency pulse comprising a spatially selective excitation radio frequency pulse.

3. The magnetic resonance method as set forth in claim 2, wherein the performing of an inversion recovery magnetic resonance excitation sequence further includes:
   after the inversion time, to maintain the substantial reduction in the magnetic resonance signal from blood, applying additional spatially non-selective inversion radio frequency pulses.

4. The magnetic resonance method as set forth in claim 1, further including:
   generating a reconstructed image from the acquired magnetic resonance signal.

5. The magnetic resonance method as set forth in claim 4, further including:
   subsequent to performing the readout magnetic resonance sequence, inducing a physiological perturbation;
   subsequent to inducing the physiological perturbation, repeating performing the magnetic resonance excitation sequence including the blood signal reduction component and performing the readout magnetic resonance sequence to acquire a second magnetic resonance signal; and
   generating a perturbation reconstructed image from the acquired second magnetic resonance signal.

6. The magnetic resonance method as set forth in claim 4, further including:
   subsequent to performing the readout magnetic resonance sequence, inducing a physiological perturbation;
   subsequent to inducing the physiological perturbation, repeating performing the magnetic resonance excitation sequence including the blood signal reduction component;
   subsequent to repeating the performing of the magnetic resonance excitation sequence including the blood signal reduction component, performing a plurality of readout magnetic resonance sequences each having a different echo time to acquire a plurality of magnetic resonance signals corresponding to the plurality of echo times;

generating a plurality of perturbation reconstructed images from the acquired plurality of magnetic resonance signals corresponding to the plurality of echo times, the determining of the microvascular blood volume parameter being based on a temporal evolution of a physiological response to the physiological perturbation based on the plurality of perturbation reconstructed images.

7. The magnetic resonance method as set forth in claim 6, wherein the determining of the microvascular blood volume parameter includes:

computing a change in vascular space occupancy signal between perturbation reconstructed images and corresponding unperturbed reconstructed images for each echo time to produce change in vascular space occupancy signal versus echo time data; and fitting the change in vascular space occupancy signal versus echo time data to a mathematical model to obtain a blood volume parameter value.

8. The magnetic resonance method as set forth in claim 4, further including:

computing a tissue magnetization based on the T1 value of the tissue;

generating a normalized reconstructed image by dividing the reconstructed image by the tissue magnetization; and estimating a blood volume parameter value based on the normalized reconstructed image.

9. The magnetic resonance method as set forth in claim 4, wherein performing the readout magnetic resonance sequence effects imaging of a subject brain region of a subject brain, and the method further includes:

providing a reference image of a reference brain region; and comparing the reconstructed image with the reference image to detect an abnormality of the subject brain region.

10. The magnetic resonance method as set forth in claim 9, wherein providing the reference image of a reference brain region includes repeating:

performing the magnetic resonance excitation sequence including the blood signal reduction component, performing the readout magnetic resonance sequence, and generating the reconstructed image on the reference brain region to generate the reference image.

11. The magnetic resonance method as set forth in claim 10, wherein the reference brain region is selected from a group consisting of:

a brain region of a contralateral side of the subject brain corresponding to the subject brain region, a brain region of a brain other than the subject brain which corresponds to the subject brain region, and a brain region of the subject brain other than the subject brain region.

12. The magnetic resonance method as set forth in claim 1, wherein performing the readout magnetic resonance sequence to acquire a magnetic resonance signal generated by the magnetic resonance excitation sequence including the blood signal reduction component includes performing one or more of:

a single-shot imaging sequence,
a single-shot echo planar sequence,
a multi-shot imaging sequence,
a spectroscopy sequence,
a multiple slice image,
a one-dimensional, two-dimensional, or three dimensional spatial encoding sequence,
a fractional k-space acquisition sequence,
a spin echo readout sequence, and
a gradient echo readout sequence.

13. A magnetic resonance system including:

a magnetic resonance imaging scanner; and a processor configured to cooperate with the magnetic resonance imaging scanner to perform a method including:

performing an inversion recovery magnetic resonance excitation sequence including a signal reduction component that reduces magnetization from blood more than magnetization from parenchymal tissue, the inversion recovery magnetic resonance excitation sequence comprising a spatially non-selective inversion recovery pulse followed by an excitation radio frequency pulse separated from the spatially non-selective inversion recovery pulse by an inversion time effective to reduce the magnetization from blood more than the magnetization from parenchymal tissue;

performing a readout magnetic resonance sequence to acquire a magnetic resonance signal generated by the magnetic resonance excitation sequence including the signal reduction component, the readout magnetic resonance sequence being performed subsequent to the performing of the inversion recovery magnetic resonance excitation sequence including the signal reduction component;

generating a reconstructed image from the acquired magnetic resonance signal; and computing a blood volume parameter value from the reconstructed image, the computing of the blood volume parameter value including at least one of:

(i) normalizing the reconstructed image based on a T1 value of tissue to generate a tissue-normalized reconstructed image and computing the blood volume from the tissue-normalized reconstructed image, and (ii) computing an intermediate parameter functionally related to blood volume for a plurality of reconstructed images produced by repetitively performing the readout magnetic resonance sequence and the generating with a corresponding plurality of echo times and fitting a parameterized model to the intermediate parameters and the corresponding echo times, the parameterized model having parameters including a rest blood volume and a blood volume change.

14. The magnetic resonance system as set forth in claim 13, wherein the computing a blood volume parameter value includes:

normalizing the reconstructed image based on a T1 value of tissue to generate a tissue-normalized reconstructed image; and computing the blood volume from the tissue-normalized reconstructed image.

15. The magnetic resonance system as set forth in claim 13, wherein the computing a blood volume parameter value includes:

computing an intermediate parameter functionally related to blood volume for a plurality of reconstructed images produced by repetitively performing the readout magnetic resonance sequence and the generating with a corresponding plurality of echo times; and fitting a parameterized model to the intermediate parameters and the corresponding echo times, the parameterized model having parameters including a rest blood volume and a blood volume change.

16. The magnetic resonance system as set forth in claim 13, wherein the method performed by the cooperating magnetic resonance imaging scanner and processor further includes:
   combining the reconstructed image with a reference image to identify an abnormality in the reconstructed image.

17. A magnetic resonance method comprising:
   acquiring a parenchymal tissue magnetic resonance signal from parenchymal tissue under different parenchymal blood volume perturbing conditions that change the vascular space occupancy within the parenchymal tissue, the acquiring including performing an inversion recovery magnetic resonance excitation sequence including a signal reduction component that reduces magnetization from blood more than magnetization from parenchymal tissue, the inversion recovery magnetic resonance excitation sequence comprising a spatially non-selective inversion recovery pulse followed by an excitation radio frequency pulse separated from the spatially non selective inversion recovery pulse by an inversion time effective to reduce the magnetization from blood more than the magnetization from parenchymal tissue; and
   determining a parenchymal vascular space occupancy-related parameter based on the acquired parenchymal tissue magnetic resonance signals.

18. The magnetic resonance method as set forth in claim 17, wherein the determining comprises:
   computing change in vascular space occupancy caused by the different parenchymal blood volume perturbing conditions.

* * * * *